(12) United States Patent
Nichols

(10) Patent No.: US 6,599,278 B1
(45) Date of Patent: Jul. 29, 2003

(54) URINARY BAG SUPPORTING DEVICE

(76) Inventor: Roy Lee Nichols, 863 Sharon Dr., Camarillo, CA (US) 93010-4947

( * ) Notice: Subject to any disclaimer, the term of this patent is extended or adjusted under 35 U.S.C. 154(b) by 0 days.

(21) Appl. No.: 10/028,528

(22) Filed: Oct. 25, 2001

(51) Int. Cl.[7] .................................................. A61F 5/44
(52) U.S. Cl. ..................................... 604/345; 604/179
(58) Field of Search ................................ 604/174, 179, 604/180, 317, 327, 332, 345, 346, 347, 353; 224/224, 226, 252, 253, 676, 663

(56) References Cited

U.S. PATENT DOCUMENTS

| | | | | |
|---|---|---|---|---|
| 1,382,446 A | * | 6/1921 | Warren | |
| 2,699,782 A | * | 1/1955 | Chester | 604/353 |
| 2,900,979 A | * | 8/1959 | Bishop | 604/327 |
| 4,122,851 A | * | 10/1978 | Grossner | 604/347 |
| 4,511,358 A | * | 4/1985 | Johnson et al. | 604/327 |
| 4,846,816 A | * | 7/1989 | Manfredi | 604/323 |
| 4,923,105 A | * | 5/1990 | Snyder | 224/255 |
| 4,957,231 A | * | 9/1990 | Kalisher | 224/583 |
| 5,026,362 A | * | 6/1991 | Willett | 604/345 |
| 5,087,251 A | * | 2/1992 | Heyman et al. | 604/327 |
| 5,135,519 A | * | 8/1992 | Helmer | 604/332 |
| 5,259,541 A | * | 11/1993 | Reese | 224/663 |
| 5,395,022 A | * | 3/1995 | Vandewall | 224/677 |
| D365,928 S | * | 1/1996 | Sauer | D3/224 |
| 5,496,282 A | * | 3/1996 | Militzer et al. | 604/179 |
| 5,590,760 A | * | 1/1997 | Astarb | 206/6 |
| 5,643,233 A | * | 7/1997 | Turner | 604/332 |
| 5,643,236 A | * | 7/1997 | Hadley | 604/353 |
| 5,716,344 A | * | 2/1998 | Kiel | 604/174 |
| 5,728,070 A | * | 3/1998 | Walker et al. | 604/179 |
| 5,776,105 A | * | 7/1998 | Corn | 604/174 |
| 5,836,497 A | * | 11/1998 | Pelish | 224/677 |
| 5,964,386 A | * | 10/1999 | Cote | 224/250 |
| 6,270,485 B1 | * | 8/2001 | Ekey | 604/345 |

* cited by examiner

Primary Examiner—Weilun Lo
Assistant Examiner—Michael Bogart
(74) Attorney, Agent, or Firm—Goldstein & Lavas P.C.

(57) ABSTRACT

A urinary bag supporting device including a plate portion. A plurality of buttons extend outwardly from the plate portion. The plurality of buttons are disposed in a spaced relationship. The buttons allow strap loops of a urinary drainage bag to be coupled therewith. A pliable clip is secured to the plate portion. The pliable clip is attachable to a belt of a wearer's pants to allow the plate portion to depend from an interior of the pants.

2 Claims, 2 Drawing Sheets

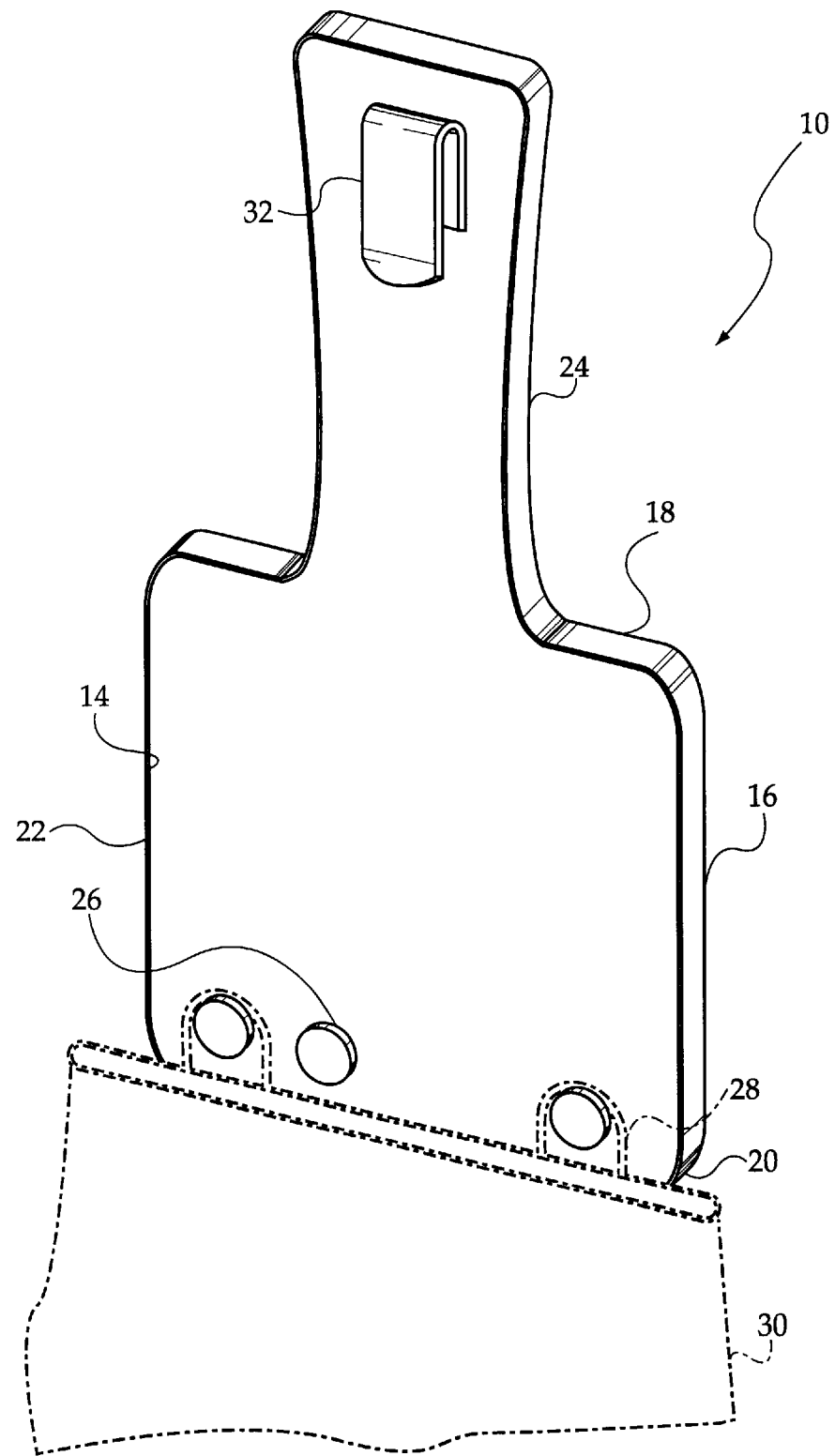

URINARY BAG SUPPORTING DEVICE

BACKGROUND OF THE INVENTION

The present invention relates to a urinary bag supporting device and more particularly pertains to supporting a urine bag from a wearer's belt interiorly of their pants.

The use of body supported medical devices is known in the prior art. More specifically, body supported medical devices heretofore devised and utilized for the purpose of supporting urinary bags are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,643,236 to Hadley discloses a urinary drain bag holder comprised of a fabric undergarment capable of being supported by the waistband and secured with buttons. U.S. Pat. No. 4,511,358 to Johnson, Jr. discloses a urine bag carrier comprised of a waist encircling belt with supporting straps with button fasteners. U.S. Pat. No. 4,846,816 to Manfredi discloses a urinary drain system supported by a waist worn belt.

While these devices fulfill their respective, particular objective and requirements, the aforementioned patents do not describe a urinary bag supporting device for supporting a urine bag from a wearer's belt interiorly of their pants.

In this respect, the urinary bag supporting device according to the present invention substantially departs from the conventional concepts and designs of the prior art, and in doing so provides an apparatus primarily developed for the purpose of supporting a urine bag from a wearer's belt interiorly of their pants.

Therefore, it can be appreciated that there exists a continuing need for a new and improved urinary bag supporting device which can be used for supporting a urine bag from a wearer's belt interiorly of their pants. In this regard, the present invention substantially fulfills this need.

SUMMARY OF THE INVENTION

In the view of the foregoing disadvantages inherent in the known types of body supported medical devices now present in the prior art, the present invention provides an improved urinary bag supporting device. As such, the general purpose of the present invention, which will be described subsequently in greater detail, is to provide a new and improved urinary bag supporting device which has all the advantages of the prior art and none of the disadvantages.

To attain this, the present invention essentially comprises a plate portion having a generally rectangular configuration. The plate portion has opposed planar front and back surfaces. The plate portion has an upper edge, a lower edge, and opposed side edges. The upper edge has an elongated neck portion extending upwardly therefrom. A plurality of buttons extend outwardly from the front surface of the plate portion upwardly of the lower edge thereof. The plurality of buttons are disposed in a spaced relationship linearly aligned with the lower edge. The buttons allow strap loops of a urinary drainage bag to be coupled therewith. A pliable clip is secured to the elongated neck portion of the plate portion. The pliable clip is attachable to a belt of a wearer's pants to allow the plate portion to depend from an interior of the pants.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved urinary bag supporting device which has all the advantages of the prior art body supported medical devices and none of the disadvantages.

It is another object of the present invention to provide a new and improved urinary bag supporting device which may be easily and efficiently manufactured and marketed.

It is a further object of the present invention to provide a new and improved urinary bag supporting device which is of durable and reliable construction.

An even further object of the present invention is to provide a new and improved urinary bag supporting device which is susceptible of a low cost of manufacture with regard to both materials and labor, and which accordingly is then susceptible of low prices of sale to the consuming public, thereby making such a urinary bag supporting device economically available to the buying public.

Even still another object of the present invention is to provide a new and improved urinary bag supporting device for supporting a urine bag from a wearer's belt interiorly of their pants.

Lastly, it is an object of the present invention to provide a new and improved urinary bag supporting device including a plate portion. A plurality of buttons extend outwardly from the plate portion. The plurality of buttons are disposed in a spaced relationship. The buttons allow strap loops of a urinary drainage bag to be coupled therewith. A pliable clip is secured to the plate portion. The pliable clip is attachable to a belt of a wearer's pants to allow the plate portion to depend from an interior of the pants.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a perspective view of the preferred embodiment of the urinary bag supporting device constructed in accordance with the principles of the present invention.

The same reference numerals refer to the same parts through the various figures.

DESCRIPTION OF THE PREFERRED EMBODIMENT

Figure 1:
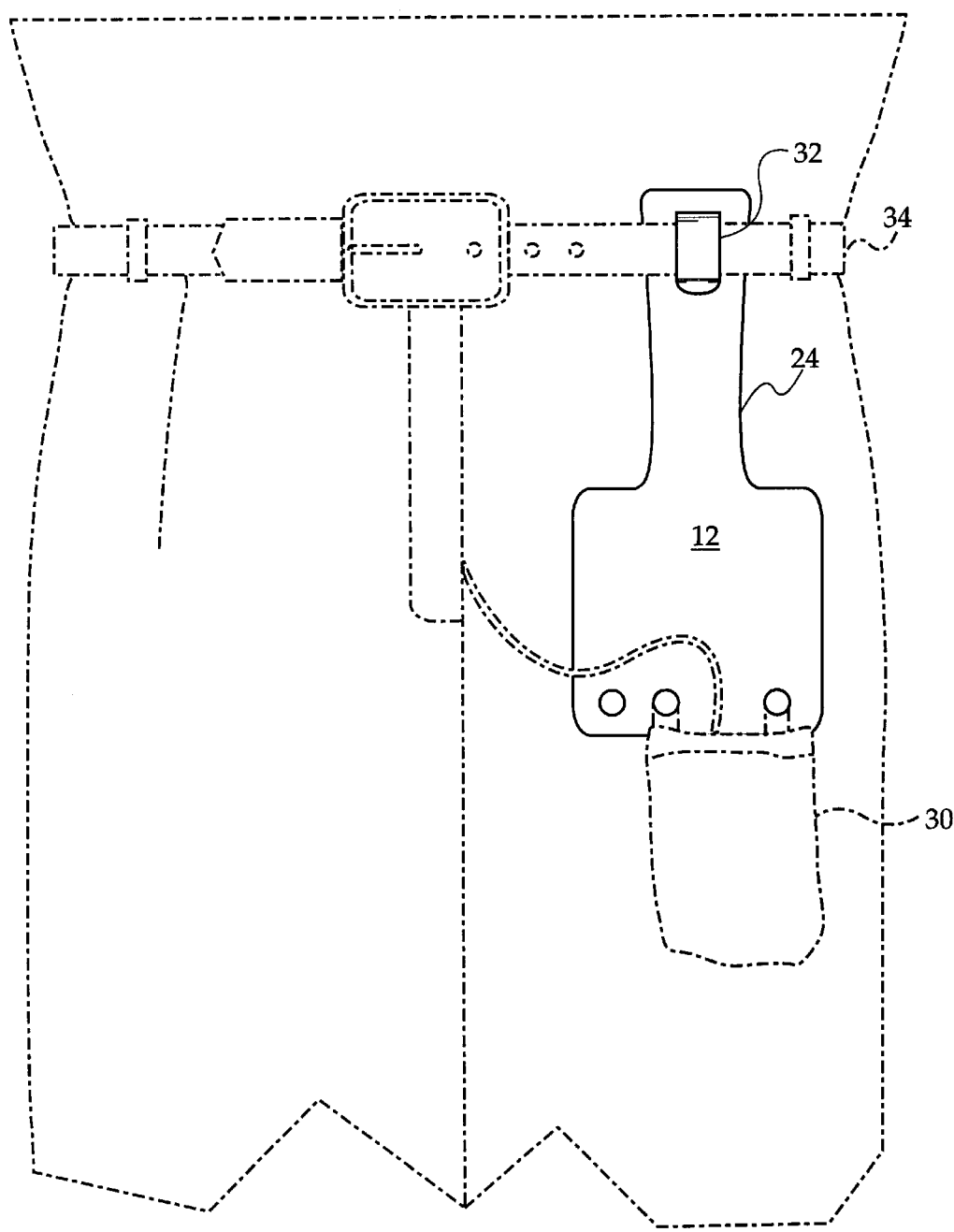
FIG. 1 is a front view of the present invention illustrated in use.

With reference now to the drawings, and in particular, to FIGS. 1 and 2 thereof, the preferred embodiment of the new and improved urinary bag supporting device embodying the principles and concepts of the present invention and generally designated by the reference number 10 will be described.

Specifically, it will be noted in the various Figures that the device relates to a urinary bag supporting device for supporting a urine bag from a wearer's belt interiorly of their pants. In its broadest context, the device consists of a plate portion, a plurality of buttons, and a pliable clip. Such components are individually configured and correlated with respect to each other so as to attain the desired objective.

The plate portion 12 has a generally rectangular configuration. The plate portion 12 has opposed planar front and back surfaces 14, 16. The plate portion 12 has an upper edge 18, a lower edge 20, and opposed side edges 22. The upper edge 18 has an elongated neck portion 24 extending upwardly therefrom. The plate portion 12 is preferably constructed of a lightweight and flexible material to allow it to be easily carried on its wearer.

The plurality of buttons 26 extend outwardly from the front surface 14 of the plate portion 12 upwardly of the lower edge 20 thereof. The plurality of buttons 26 are disposed in a spaced relationship(linearly aligned with the lower edge 20. The buttons 26 allow strap loops 28 of a urinary drainage bag 30 to be coupled therewith. The use of multiple buttons 26 will accommodate different sized urinary bags.

The pliable clip 32 is secured to the elongated neck portion 24 of the plate portion 12. The pliable clip 32 is attachable to a belt 34 of a wearer's pants to allow the plate portion 12 to depend from an interior of the pants. Alternately, the clip 32 can merely be attached to the waistband of the pants.

The present invention will replace the elastic straps that hold urinary drainage bags to a leg of users. The present invention will eliminate the worries that are associated with these straps, particularly the risk of the bag sliding down the leg.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A urinary bag supporting device for supporting a urine bag from a wearer's belt interiorly of their pants comprising, in combination:

a plate portion having a generally rectangular configuration, the plate portion having opposed planar front and back surfaces, the plate portion having an upper edge, a lower edge, and opposed side edges, the upper edge having an elongated neck portion extending upwardly therefrom;

a plurality of buttons extending outwardly from the front surface of the plate portion upwardly of the lower edge thereof, the plurality of buttons being disposed in a spaced relationship linearly aligned with the lower edge, the buttons allowing strap loops of a urinary drainage bag to be coupled therewith; and a pliable clip secured to the elongated neck portion of the plate portion, the pliable clip being attachable to a belt of a wearer's pants to allow the plate portion to depend from an interior of the pants.

2. A urinary bag supporting device for supporting a urine bag from a wearer's belt interiorly of their pants comprising, in combination:

a plate portion;

a plurality of buttons extending outwardly from the plate portion, the plurality of buttons being disposed in a spaced relationship, the buttons allowing strap loops of a urinary drainage bag to be coupled therewith; and a pliable clip secured to the plate portion, the pliable clip being attachable to a belt of a wearer's pants to allow the plate portion to depend from an interior of the pants.

\* \* \* \* \*